United States Patent [19]

Fleischle

[11] Plant 4,946

[45] Nov. 16, 1982

[54] DISTINCT VARIETY OF STREPTOCARPUS NAMED LADY

[75] Inventor: Gerhard Fleischle, Vaihingen, Fed. Rep. of Germany

[73] Assignee: Oglevee Associates, Inc., Connellsville, Pa.

[21] Appl. No.: 204,346

[22] Filed: Nov. 5, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Webb, Burden, Robinson & Webb

[57] ABSTRACT

A new variety of Streptocarpus plant is characterized by its pink flower having a light rose throating and its compact habit.

1 Drawing Figure

BACKGROUND OF THE NEW PLANT

The present invention comprises a new and distinct cultivar of *Streptocarpus* × *hybridus* known by the varietal name Lady. The new cultivar is a mutation achieved through irradiation of Marna, formerly named Neptune Blue (U.S. Plant Pat. No. 4,524).

The new cultivar is most similar to Marna. However, Lady is more compact, having smaller foliage and more leaves. In addition, the overall color of Lady is different from Marna with Lady being pink and having a light yellow throating, which is discernible from a distance.

The new cultivar was discovered in 1979 in Vaihingen, Federal Republic of Germany; was first asexually reproduced by cuttings in Vaihingen, Federal Republic of Germany; and has been asexually reproduced by cuttings at Oglevee Floral Company in Connellsville, Pa. It has been found to retain its distinctive characteristics through successive propagations.

DESCRIPTION OF THE DRAWING

The accompanying drawing illustrates the new cultivar.

DESCRIPTION OF THE NEW PLANT

The following detailed description sets forth the characteristics of the new cultivar. The data which defines these characteristics were collected from asexual reproductions carried out by Gerhard Fleischle at Vaihingen, Federal Republic of Germany. Color references are primarily to the R.H.S. color chart of the Royal Horticultural Society of London unless otherwise referenced.

The color references were collected from asexual reproductions carried out by Oglevee Floral Company in Connellsville, Pa.

Botanical classification: Gesneriaceae (Family); *Streptocarpus* × *hybridus* (Genus × Species).

Flower:

*Fully expanded.*—Five centimeters.

*Borne.*—In clusters of one to six flowers per flower stalk above the foliage. Flower stalks arise from mid-rib of each leaf.

*Stems.*—Single, long and pubescent.

*Form.*—Funnel formed in an umbel.

Color:

*Front of petal.*—Fan 2 Red Purple Group 65-C.

*Throat.*—Fan 1 Yellow Group 4-C with sparse striping, Fan 2 Red Purple Group 66-B.

*Base of petal.*—Fan 2 Red Purple Group 65-C.

*Reverse of petal.*—Fan 2 Red Purple Group 65-C.

*Tonality from a distance.*—Exotica 37 Rose Pink.

*Discoloration.*—Insignificant.

Petals:

*Texture.*—Velvet.

*Appearance.*—Individually lobed and smooth margin.

*Arrangement.*—Regularly united into an elliptical form.

*Fragrance.*—None.

Reproductive organs:

*Anthers.*—Two per flower and interconnected.

*Pollen.*—Generally nonfertile.

Plant:

*Form.*—Leaves rosulete from a crown at the soil line.

*Growth.*—A spreading, free flowing habit with leaf bases being acute.

*Height from soil line.*—12 to 18 centimeters.

*Spread.*—30 to 35 centimeters.

Foliage:

*Size.*—Approximately 17 centimeters in length and 3 to 8 centimeters in width at the widest point.

*Shape.*—Oblanceolete.

*Topside.*—Fan 3 Green Group 137-B.

*Underside.*—Fan 3 Green Group 142-C.

*Quantity.*—10 to 18 leaves.

*Underside.*—Fan 4 Gray Green Group.

*Ribs and veins.*—Pinnate.

*Rib and vein color.*—Fan 3 Green Group 139-D.

*Margin.*—Crenate serrations.

*Stipules.*—None.

I claim:

1. A new and distinct variety of Streptocarpus substantially as herein shown and described.

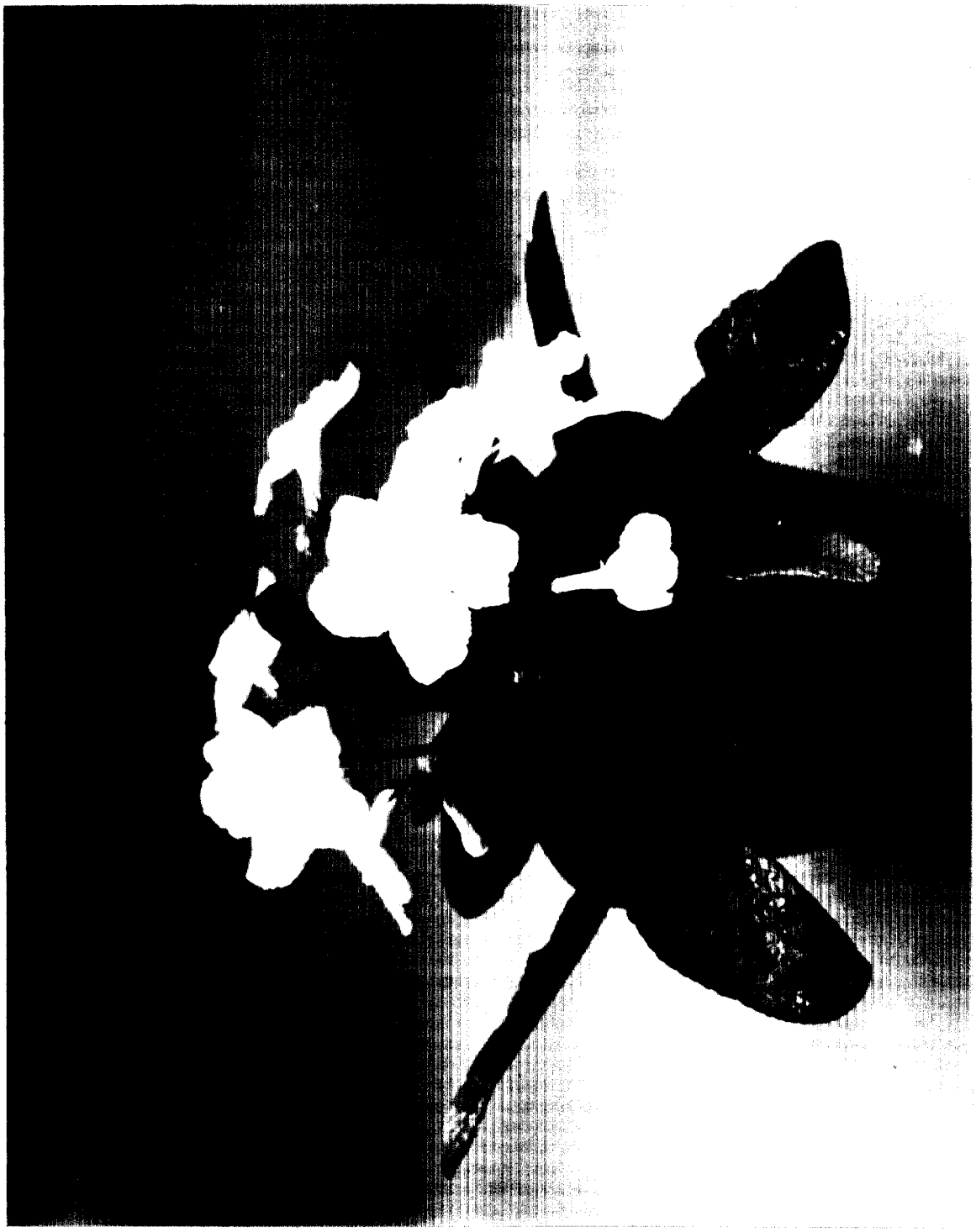

* * * * *